US012042555B2

United States Patent
Varanasi et al.

(10) Patent No.: US 12,042,555 B2
(45) Date of Patent: Jul. 23, 2024

(54) ANTI-STAIN ORAL CARE COMPOSITION

(71) Applicant: BASF SE, Ludwigshafen (DE)

(72) Inventors: Padma P. Varanasi, Wyandotte, MI (US); Lu Zhang, Tarrytown, NY (US); Leonora Ethleen Leigh, Tarrytown, NJ (US); Liliana Craciun, Budd Lake, NJ (US); Adrian Natalello, Ludwigshafen (DE); Joseph Lupia, Florham Park, NJ (US)

(73) Assignee: BASF SE, Ludwigshafen Am Rhein (DE)

( * ) Notice: Subject to any disclaimer, the term of this patent is extended or adjusted under 35 U.S.C. 154(b) by 55 days.

(21) Appl. No.: 16/963,616

(22) PCT Filed: Jan. 22, 2019

(86) PCT No.: PCT/IB2019/000147
§ 371 (c)(1),
(2) Date: Jul. 21, 2020

(87) PCT Pub. No.: WO2019/145794
PCT Pub. Date: Aug. 1, 2019

(65) Prior Publication Data
US 2021/0059923 A1    Mar. 4, 2021

Related U.S. Application Data

(60) Provisional application No. 62/621,309, filed on Jan. 24, 2018.

(51) Int. Cl.
*A61K 8/81* (2006.01)
*A61K 8/24* (2006.01)
*A61Q 11/00* (2006.01)

(52) U.S. Cl.
CPC ............. *A61K 8/8147* (2013.01); *A61K 8/24* (2013.01); *A61Q 11/00* (2013.01)

(58) Field of Classification Search
CPC . A61K 6/083; A61K 6/02; A61K 7/16; A61K 8/81; A61Q 11/00
USPC ........................................ 106/35; 424/49, 57
See application file for complete search history.

(56) References Cited

U.S. PATENT DOCUMENTS

| | | |
|---|---|---|
| 3,635,915 A | 1/1972 | Gale |
| 3,755,264 A | 8/1973 | Testa |
| 4,175,066 A | 11/1979 | Shibazaki et al. |
| 4,390,670 A | 6/1983 | Walinsky |
| 4,547,559 A | 10/1985 | Walinsky |
| 4,621,127 A | 11/1986 | Denzinger et al. |
| 4,710,537 A | 12/1987 | Walinsky |
| 4,725,655 A | 2/1988 | Denzinger et al. |
| 4,842,847 A | 6/1989 | Amjad |
| 4,857,303 A | 8/1989 | Grollier |
| 4,892,724 A | 1/1990 | Amjad |
| 4,892,725 A | 1/1990 | Amjad |
| 4,914,167 A | 4/1990 | Hambrecht et al. |
| 5,011,682 A * | 4/1991 | Elliott ................. A61K 8/8164 424/52 |
| 5,013,541 A | 5/1991 | Elliott et al. |
| 5,015,467 A | 5/1991 | Smitherman |
| 5,135,677 A | 8/1992 | Yamaguchi et al. |
| 5,143,719 A | 9/1992 | Elliott et al. |
| 5,175,361 A | 12/1992 | Denzinger et al. |
| 5,194,246 A | 3/1993 | Vincent et al. |
| 5,213,789 A | 5/1993 | Degenhardt et al. |
| 5,244,988 A | 9/1993 | Hughes et al. |
| 5,292,501 A | 3/1994 | Degenhardt et al. |
| 5,414,060 A | 5/1995 | Humphries et al. |
| 5,601,723 A | 2/1997 | Kirk et al. |
| 5,866,012 A | 2/1999 | Austin et al. |
| 5,925,610 A | 7/1999 | Austin et al. |
| 6,034,152 A | 3/2000 | Burger et al. |
| 6,133,343 A | 10/2000 | Hatanaka et al. |
| 6,335,404 B1 | 1/2002 | Kirk et al. |
| 6,905,672 B2 | 6/2005 | Rajaiah et al. |
| 9,271,906 B2 | 3/2016 | Miller et al. |
| 2001/0037750 A1* | 11/2001 | Miyama ................... A61K 6/20 106/35 |
| 2015/0118166 A1* | 4/2015 | Sagel ....................... A61K 8/86 424/49 |
| 2016/0324738 A1 | 11/2016 | Baig et al. |
| 2016/0324741 A1* | 11/2016 | Baig ..................... A61K 8/8147 |
| 2017/0151158 A1 | 6/2017 | Myers et al. |

FOREIGN PATENT DOCUMENTS

| | | |
|---|---|---|
| DE | 3213296 A1 | 12/1982 |
| DE | 3147489 A1 | 6/1983 |
| EP | 0075820 A1 | 4/1983 |
| EP | 0106110 A1 | 4/1984 |
| EP | 400858 A2 | 12/1990 |
| EP | 523776 A2 | 1/1993 |

(Continued)

OTHER PUBLICATIONS

Dow, "Acusol 497N." www.dow.com>pdp.acusol-497n.182480z.html. published online Sep. 14, 2019 (Year: 2019).*
International Search Report and Written Opinion dated May 27, 2019 for Application No. PCT/IB2019/000147, 14 pages.
Examination Report for IN202027032414 dated May 24, 2021, 8 page.
International Search Report for PCT/IB2019/000147 dated May 27, 2019, 4 pages.

(Continued)

*Primary Examiner* — Walter E Webb
(74) *Attorney, Agent, or Firm* — Lowenstein Sandler LLP (57) ABSTRACT

The present invention discloses an oral care composition for the prevention or minimization of stain formation on a tooth surface as well as an oral care composition for prevention or reduction of existing stains from, a tooth surface.

13 Claims, 5 Drawing Sheets

(56) References Cited

FOREIGN PATENT DOCUMENTS

| EP | 0985690 | A2 | 3/2000 |
|---|---|---|---|
| JP | 2000247851 | A | 9/2000 |
| WO | 1991006280 | | 5/1991 |
| WO | 9416673 | A1 | 8/1994 |
| WO | 94016673 | A1 | 8/1994 |
| WO | 9912517 | A1 | 3/1999 |
| WO | 99012517 | A1 | 3/1999 |
| WO | 2015171837 | A1 | 11/2015 |

OTHER PUBLICATIONS

Khamdo DY, Khanlarov TG, Ayubova AM, Ganbarov DG; "Complexation of metal ions with the copolymer of maleic and acrylic acids"; Journal of Analytical Chemistry 1993, 48(3), 313-316.

Pesonen H, Sillanpa A, Aksela R, Laasonen K; "Density functional complexation study of metal ions with poly (carboxylic acid) ligands. Part 2. Poly(acrylic acid-co-maleic acid), poly(methyl vinyl ether-co-maleic acid), and poly (epoxy succinic acid)"; Polymer 2005, 46, 12653-12661.

Yoshida Y, Van Meerbeek B, Nakayama Y; "Evidence of Chemical Bonding at Biomaterial-Hard Tissue Interfaces"; Journal of Dental Research 2000, 79(2), 709-713.

Fukuda R, Yoshida Y, Nakayama Y, Okazaki M, Inoue S, Sano H, Suzuki K, Shintani H, Van Meerbeek B; "Bonding efficacy of polyalkenoic acids to hydroxyapatite, enamel and dentin"; Biomaterials 2003, 24(11), 1861-1867.

Zhang SG, Wang FY, Tan XY; "Molecular dynamics simulation of the hydroxyapatite scale inhibition mechanism of water-soluble polymers"; Journal of Theoretical and computational Chemistry 2010, 9(5), 889-902.

Akinmade AO, Nicholson JW; "Glass-ionomer cements as adhesives. Part I Fundamental aspects and their clinical relevance"; Journal of Materials Science: Materials in Medicine 1993, 4, 95-101.

Nicholson JW, Abiden F; "Changes in compressive strength on ageing in glass polyalkenoate (glass-ionomer) cements prepared from acrylic/maleic acid copolymers"; Biomaterials 1997, 18, 59-62.

Culbertson BM; "New polymeric materials for use in glass-ionomer cements"; Journal of Dentistry 2006, 34(8), 556-565.

Nicholson JW; "Adhesion of glass-ionomers cements to teeth: a review"; International Journal of Adhesion and Adhesives 2016, 69, 33-38.

Nathoo SA; "The chemistry and mechanisms of extrinsic and intrinsic discoloration"; Journal of the American Dental Association 1997, 128, Supplement S, S6-S10.

Watts A, Addy M; "Tooth discoloration and staining: a review of the literature"; British Dental Journal 2001, 190(6), 309-316.

Addy M, Moran J; "Mechanisms of stain formation on teeth, in particular associated with metal ions and antiseptics"; Advances in Dental Research 1995, 9, 450-456.

Abdallah MN, Light N, Amin WM, Retrouvey JM, Cerruti M, Tamimi F; "Development of a composite resin disclosing agent based on the understanding of tooth staining mechanisms"; Journal of Dentistry 2014, 42, 697-708.

Technical Data Sheet, The Dow Chemical Company, Acusol 445 Detergent Polymer for Laundry, 2020, 5 pages.

Technical Data Sheet, The Dow Chemical Company, Acusol 460 Dispersant Polymer, 2020, 3 pages.

Technical Data Sheet, The Dow Chemical Company, Acusol 448 Dispersant Polymer, 2020, 3 pages.

Office Action for Japanese Patent Application No. JP2020-540488 dated Oct. 31, 2023, 20 pages.

\* cited by examiner

ANTI-STAIN ORAL CARE COMPOSITION

CROSS-REFERENCE TO RELATED APPLICATION(S)

This application is a national phase of International Application No. PCT/IB2019/000147, filed on Jan. 22, 2019, which claims the benefit of U.S. Provisional Patent Application No. 62/621,309, filed on Jan. 24, 2018. The contents of these applications are hereby incorporated by reference in their entirety.

FIELD OF THE INVENTION

The present invention relates to oral care compositions, methods of their use, and methods of their preparation. Particularly to oral care compositions for preventing or minimizing stain formation on the tooth surface and for preventing or reducing existing stains on the tooth surface.

BACKGROUND OF THE INVENTION

Efforts to whiten teeth have a long history, thought to date back to the Ancient Egyptians. Indeed, even nowadays there is a widespread market for teeth whitening products and whiter teeth are often associated with increased confidence and self-esteem. Modern science has provided a detailed understanding of the factors that contribute to tooth color, which has enabled improved products and methods for whitening teeth. The normal shade of teeth is determined by the natural off-white tints of the enamel and the dentin beneath. However, extrinsic and intrinsic staining also contributes to the shade of teeth.

Extrinsic or direct staining refers to surface stains, such as those caused by chromogens from tea, coffee, red wine, and other foods rich in polyphones which consumers use on a daily basis. Direct or extrinsic dental stains may also be caused due to increased accumulation or chemical modification (metal bridging, denaturation, etc) of the bacterial pellicle proteins. Extrinsic stains are physically removed from the tooth surface through the use of surfactants and/or abrasives (e.g., in toothpaste) which aid in the stain removal process by disrupting the pellicle/plaque matrix and preventing its accumulation.

Intrinsic staining refers to stains that exist below the enamel surface, or that penetrate below the enamel surface. Intrinsic staining can happen when food molecules seep into enamel flaws and cracks, or, in some cases, between enamel rods. Intrinsic discoloration can also occur following a change to the structural composition or thickness of the dental hard tissues. Certain metabolic diseases and tooth trauma can also cause intrinsic staining.

Removal of intrinsic staining is more difficult and time consuming than removal of extrinsic staining. Intrinsic stain removal can be achieved by a variety of methods including use of peroxides or peroxide analogs, with or without chemical, light or heat activation, to bleach the stains or to solubilize the chromogens. This method oxidizes organic compounds within the enamel and dentin, thereby changing colored materials to non-colored materials; it does not remove the stain itself. Acids and dehydration methods, which lead to opacification of enamel to obscure the subsurface stains, are also used to remove or mask intrinsic staining.

Tooth whitening products are available over-the-counter and as professional services in a dentist's office. These products typically contain abrasives such as peroxide agents and pyrophosphate salts. Prolonged use of these products, could result in several unpleasant side effects, including tooth sensitivity, soft tissue irritation and tooth surface changes. Accordingly, there is a need in the art for safer and gentler tooth whitening oral care composition.

SUMMARY

It is an object of certain embodiments of the disclosure to provide an oral care composition for preventing or minimizing the formation of stains on a tooth surface.

It is an object of certain embodiments of the disclosure to provide an oral care composition for removing or reducing existing stains from a tooth surface.

It is an object of certain embodiments of the disclosure to provide a method for preventing or minimizing the formation of stains on a tooth surface.

It is an object of certain embodiments of the disclosure to provide a method for removing or reducing existing stains from a tooth surface.

It is an object of certain embodiments of the disclosure to provide a method for preparing an oral care composition for preventing or minimizing the formation of stains on a tooth surface.

It is an object of certain embodiments of the disclosure to provide a method for preparing an oral care composition for removing or reducing existing stains from a tooth surface.

It is an object of certain embodiments of the disclosure to provide a kit with an oral care composition for preventing or minimizing the formation of stains on a tooth surface.

It is an object of certain embodiments of the disclosure to provide a kit with an oral care composition for preventing or reducing existing stains from a tooth surface.

The above objects of the present invention and others may be achieved by the present invention which in certain embodiments is directed to an oral care composition comprising at least one acrylic acid-maleic acid (AA-MA) copolymer and a pharmaceutically acceptable excipient.

In some embodiments, the present invention is directed to an effective amount of at least one AA-MA copolymer or a salt thereof to prevent or minimize formation of stains on a tooth surface and a pharmaceutically acceptable excipient.

In some embodiments, the present invention is directed to an effective amount of at least one AA-MA copolymer or a salt thereof to remove or reduce existing stains from a tooth surface and a pharmaceutically acceptable excipient.

In some embodiments, the present invention is directed to a method for preventing or minimizing stain formation on a tooth surface. In some embodiments, the present invention is directed to a method for preventing or reducing existing stains from a tooth surface. These methods may comprise treating the tooth surface with an oral care composition comprising at least one AA-MA copolymer or a salt thereof and a pharmaceutically acceptable excipient. In some embodiments, the methods disclosed herein may comprise treating the tooth surface with an oral care composition comprising an effective amount of at least one AA-MA copolymer or a salt thereof to prevent or minimize stain formation on the tooth surface and a pharmaceutically acceptable excipient. In some embodiments, the methods disclosed herein may comprise treating the tooth surface with an oral care composition comprising an effective amount of at least one AA-MA copolymer or a salt thereof to prevent or reduce existing stains from the tooth surface and a pharmaceutically acceptable excipient.

In some embodiments, the present invention is directed to a method for preparing an oral care composition according to an embodiment. The method may comprise forming an aqueous polymer solution comprising at least one AA-MA copolymer or a salt thereof. The method may further comprise combining the aqueous polymer solution with a pharmaceutically acceptable excipient.

In some embodiments, the present invention is directed to a kit with an oral care composition according to an embodiment. The kit may further comprise instructional materials.

BRIEF DESCRIPTION OF THE DRAWINGS

The above and other features of the present disclosure, their nature, and various advantages will become more apparent upon consideration of the following detailed description, taken in conjunction with the accompanying drawings, in which.

DETAILED DESCRIPTION

Oral Care Composition

In some embodiments, the present disclosure is directed to oral care compositions suitable for preventing or minimizing the formation of new stains on a tooth surface. In some embodiments, the present disclosure is directed to oral care compositions suitable for preventing or reducing the appearance of existing stains on a tooth surface. The present disclosure is directed to a long-lasting tooth whitening remedy which may be utilized for preventing or minimizing new stains or for preventing or reducing existing stains from the tooth surface. The remedy may provide for a mild and sustainable approach that protects the enamel of the teeth from acids (e.g., by providing a barrier to the tooth surface) and by minimizing gum irritation, sensitization, and sloughing of the epithelium as compared to more aggressive technologies that are being presently used.

In some embodiments, the present disclosure is directed to an oral care composition comprising a polymer alone, such as an AA-MA copolymer. In other embodiments, the present disclosure is directed to a combination of a polymer, such as an AA-MA copolymer, and a pyrophosphate salt and/or another pharmaceutically acceptable excipient. In some embodiment, the oral care composition contemplated herein may bind onto the surface of the tooth enamel, thereby providing a barrier (e.g., a film barrier) that can prevent stains from adsorbing onto the tooth surface (e.g., by physically protecting against the binding of chromogens or bacterial pellicle). In certain embodiments, the polymer may bind to the tooth surface and act as a sealant to prevent bacterial adsorption. By binding and being retained on the tooth surface, the polymers may provide a long lasting effect on the prevention and/or reduction and/or removal of stains and bacteria accumulation on the tooth surface. The polymers discussed herein may also assist in removing calcium or other ions in the saliva that play a role in stain formation. For instance, the polymers discussed herein may (in addition to calcium ions) complex $Fe^{+3}$ ions, thereby preventing them from catalyzing the denaturation of the pellicle proteins which would otherwise cause discoloration.

Suitable AA-MA copolymers for the oral care composition may be present in a salt form. Salts of AA-MA copolymers may include a sodium salt of AA-MA copolymer, a potassium salt of AA-MA copolymer and other conceivable salts understood by one of ordinary skill in the art as being suitable for treating a tooth surface.

Exemplary AA-MA copolymers in their sodium salt form may have the following chemical structure:

AA-MA copolymers are water soluble, flexible and clear film formers, making them suitable for use in adhesives or coatings where they may improve the adhesion of metal surfaces by metal complexation with the carboxylic group in the copolymer. The hydrophilicity and metal ion chelating ability of the polymers makes them suitable for applications in aqueous systems as anti-scaling agents, encrustation inhibitors, viscosity modifiers, for fiber sizing, or as detergent aids for stain removal.

In the sodium salt form, the AA-MA copolymer chain is extended due to the electrostatic charge repulsions between the negatively charged carboxylic groups, leaving the carboxylic groups "exposed" and easily accessible for complexation. Without being bound to theory, it is believed that the carboxylic groups of the AA-MA copolymer form hydrogen bonds with the layer of the tightly bound water on the surface of the tooth and that these hydrogen bonds are gradually replaced by ionic bonds formed between the carboxylate groups and the calcium ions in the tooth. Thus, the adhesiveness of the AA-MA copolymer to dentin/enamel may be due to the copolymer's complexation of $Ca^{+2}$ from hydroxyapatite $[Ca_{10}(PO_4)_6(OH)_2]$ by the carboxylic groups in the copolymer and potentially due to the copolymer's diffusion into the softened tooth surface, which may enable and aid in removal of intrinsic stains.

In certain embodiments, about two thirds of the carboxylic groups in the AA-MA copolymer may be bound to hydroxyapatite. In some embodiments, about one quarter or more, about one third or more, about one half or more, about two thirds or more, or substantially all of the carboxylic groups in the AA-MA copolymer may be bound to hydroxyapatite.

In certain embodiments about 0.05 wt % or more, about 0.1 wt % or more, about 0.15 wt % or more, about 0.2 wt % or more, about 0.25 wt % or more, about 0.3 wt % or more, about 0.35 wt % or more, about 0.4 wt % or more, about 0.45 wt % or more, about 0.5 wt % or more of the $Ca^{+2}$ ions may be extracted by an AA-MA copolymer based on total weight of $Ca^{+2}$ in the hydroxyapatite. In some embodiments, a copolymer of AA-MA may decalcify the hydroxyapatite more rapidly than an acrylic acid homopolymer.

Oral care composition according to embodiments may comprise at least one AA-MA copolymer or a salt thereof and a pharmaceutically acceptable excipient. In certain embodiments, the oral care composition may comprise an effective amount of at least one AA-MA copolymer or a salt thereof to prevent or minimize formation of stains on a tooth surface. In certain embodiments, the oral care composition may comprise an effective amount of at least one AA-MA copolymer or a salt thereof to remove or reduce existing stains from a tooth surface.

Suitable AA-MA copolymers may have a molecular weight ranging from about 5,000 g/mol to about 300,000 g/mol, from about 15,000 g/mol to about 200,000 g/mol, from about 30,000 g/mol to about 100,000 g/mol, from about 40,000 g/mol to about 80,000, from about 45,000 g/mol to about 75,000, about 50,000 g/mol, or about 70,000 g/mol. In some embodiments, higher molecular weight polymers may adhere better to a tooth surface.

Suitable AA-MA copolymers may also have a molar ratio of AA to MA ranging from about 1:50 to about 50:1, from about 1:30 to about 30:1, from about 1:20 to about 20:1, from about 1:10 to about 10:1, from about 1:9 to about 9:1, from about 1:1 to about 10:1, from about 1:1 to about 9:1, from about 1:1 to about 5:1, from about 1:1 to about 4:1, from about 1:1 to about 3:1, about 1:0.6, or about 1:0.3.

In some embodiments, the oral care compositions disclosed herein may comprise a pharmaceutically acceptable excipient, including but not limited to, a solvent, a thickener, a buffer, a humectant, a surfactant, an abrasive, a sweetener, a flavorant, a pigment, a dye, an anti-caries agent, an anti-bacterial agent, a whitening agent, a desensitizing agent, a preservative, or a mixture thereof. In some embodiments, the oral care composition may comprise from about 10 wt % to about 99.9 wt %, from about 30 wt % to about 99.7 wt %, from about 50 wt % to about 99.5 wt %, from about 60 wt % to about 99 wt %, from about 70 wt % to about 98 wt %, from about 80 wt % to about 97 wt %, from about 90 wt % to about 99.99 wt %, from about 92 wt % to about 99.9 wt %, from about 95 to about 99.7 wt %, from about 97 wt % to about 99.5 wt %, from about 98.8 to about 99.4, about 99.3, about 99.2, about 99.1, about 98.9, about 97 wt %, about 98 wt %, or about 99 wt % of a pharmaceutically acceptable excipient.

In certain embodiments, the pharmaceutically acceptable excipient may comprise pyrophosphate or salts thereof. In some embodiments, the oral care composition may comprise from about 0.1 wt % to about 20 wt %, from about 0.3 wt % to about 10 wt %, from about 0.5 wt % to about 5 wt %, from about 1 wt % to about 3 wt %, about 1 wt %, or about 2 wt % pyrophosphates, salts thereof, or any other pharmaceutically acceptable excipient. Suitable pyrophosphate salts may comprise sodium pyrophosphate, potassium pyrophosphate, other salts of pyrophosphates understood by one of ordinary skill in the art as being suitable for an oral care composition, and combinations thereof.

Oral care compositions contemplated herein include, but are not limited to, pure polymer solutions, a mouth wash, a toothpaste, an orally dissolving strip, a whitening gel, a whitening wrap, a whitening cream, a whitening ointment, and other conceivable oral care products or treatment solutions understood by one of ordinary skill in the art as being suitable for treating a tooth surface. Oral compositions contemplated herein may have a neutral taste in certain embodiments.

In certain embodiments, oral care compositions disclosed herein have a pH ranging from about 5 to about 9, from about 6 to about 8.5, about 5, about 5.5, about 6, about 6.5, about 7, about 7.5, about 8, about 8.5, or about 9.

In certain embodiments, the oral care composition may comprise from about 0.1 wt % to about 10 wt %, from about 0.3 wt % to about 8 wt %, from about 0.5 wt % to about 5 wt %, from about 1 wt % to about 3 wt %, about 1 wt %, or about 2 wt % aqueous polymer solution based on total weight of the oral care composition.

The pH of the 2 wt % polymer solution may have a range of about 7-10, about 8-9, about 8-8.5, about 8, about 8.1, about 8.2, about 8.3, about 8.4, or about 8.5.

The aqueous polymer solution may comprise at least one AA-MA copolymer or a salt thereof at a concentration of about 10-70% by weight, 20%-60% by weight, about 30%-50% by weight, about 35%-45% by weight, or about 40% by weight of the at least one AA-MA copolymer or a salt thereof based on total weight of the aqueous polymer solution.

In some embodiments, the oral care composition may comprise granules of the at least one AA-MA copolymer or salt thereof. The granules may comprise from about 70 wt % to about 100 wt %, from about 75 wt % to about 95 wt %, from about 80 wt % to about 95 wt %, from about 85 wt % to about 95 wt %, from about 90 wt % to about 95 wt %, about 90 wt %, about 91 wt %, about 92 wt %, about 93 wt %, about 94 wt %, or about 95 wt % of the at least one AA-MA copolymer or salt thereof based on total weight of the granules.

In some embodiments, the oral care composition may comprise from about 0.01 wt % to about 10 wt %, from about 0.1 wt % to about 5 wt %, from about 0.3 wt % to about 3 wt %, from about 0.5 wt % to about 2 wt %, from about 0.6 wt % to about 1.2 wt %, about 0.7 wt %, about 0.8 wt %, about 0.9 wt %, about 1 wt %, or about 1.1 wt % of the at least one AA-MA copolymer or a salt thereof based on total weight of the oral care composition.

In one embodiment, the oral care composition may comprise 0.8 wt % of AA/MA Copolymer A (a sodium salt of an AA-MA copolymer having a molecular weight of 70,000 g/mol and a molar ratio of acrylic acid to maleic acid of 1:0.3) and may have a pH of about 8, the wt % being based on the total weight of the oral care composition.

In one embodiment, the oral care composition may comprise 0.8 wt % of AA/MA Copolymer B (a sodium salt of an AA-MA copolymer having a molecular weight of 50,000 g/mol and a molar ratio of acrylic acid to maleic acid of 1:0.6) and may have a pH of about 8, the wt % being based on the total weight of the oral care composition.

In one embodiment, the oral care composition may comprise: i) 2 wt % of a sodium salt of an AA-MA copolymer having a molecular weight of 70,000 g/mol and a molar ratio of acrylic acid to maleic acid of 1:0.3 (AA/MA Copolymer A); ii) 1 wt % of potassium pyrophosphate; and iii) 1 wt % of sodium pyrophosphate, and the oral care composition may have a pH of about 5.5.

In one embodiment, the oral care composition may comprise: i) 2 wt % of a sodium salt of an AA-MA copolymer having a molecular weight of 50,000 g/mol and a molar ratio of acrylic acid to maleic acid of 1:0.6 (AA/MA Copolymer B); ii) 1 wt % of potassium pyrophosphate; and iii) 1 wt % of sodium pyrophosphate, and the oral care composition may have a pH of about 5.5.

Method of Treatment and Preparation

In some embodiments, the present disclosure is directed to a method for preventing or minimizing the formation of new stains on a tooth surface. In some embodiments, the present disclosure is directed to a method for preventing or reducing the appearance of existing stains on a tooth surface.

Methods according to embodiments may comprise treating the tooth surface with an oral composition in accordance with embodiments disclosed herein. In some embodiments, treating the tooth surface may comprise applying, brushing, rinsing, spraying, pouring, and combinations thereof, an oral care composition, in accordance with embodiments, onto the tooth surface or onto the vicinity of the tooth surface. In one embodiment, treating the tooth surface comprises brushing the tooth surface with an oral care composition (e.g., a toothpaste). In one embodiment, treating the tooth surface may comprise rinsing the mouth, i.e. the vicinity of a tooth surface, with an oral care composition (e.g., a mouthwash).

In some embodiments, treating a tooth surface with an oral care composition according to embodiments yields a lightness L* for the tooth surface that is about 30 or greater, about 35 or greater, about 40 or greater, about 45 or greater, about 50 or greater, about 55 or greater, about 60 or greater, about 70 or greater, ranges from about 30 to about 80, from about 35 to about 80, from about 40 to about 80, from about 45 to about 80, from about 50 to about 80, from about 30 to about 75, from about 35 to about 75, from about 40 to about 75, from about 45 to about 75, from about 50 to about 75, from about 30 to about 70, from about 35 to about 70, from about 40 to about 70, from about 45 to about 70, from about 50 to about 70, from about 50 to about 75, from about 50 to about 85, from about 50 to about 90, from about 60 to about 75, from about 60 to about 85, from about 60 to about 90, from about 60 to about 95, from about 70 to about 75, from about 70 to about 85, from about 70 to about 90, or from about 70 to about 95.

In some embodiments, treating a tooth surface with an oral care composition according to embodiments yields a Delta E* for the tooth surface that is about 60 or lower, about 55 or lower, about 50 or lower, about 45 or lower, about 40 or lower, about 35 or lower, about 30 or lower, about 25 or lower, about 20 or lower, from about 20 to about 60, from about 20 to about 50, from about 20 to about 40, from about 20 to about 30, from about 30 to about 60, from about 30 to about 50, from about 30 to about 40, from about 40 to about 60, from about 40 to about 50, or from about 50 to about 60.

In some embodiments, the present disclosure is directed to a method for preparing an oral care composition according to embodiments. The method may comprise forming an aqueous polymer solution and combining (e.g., diluting) the aqueous polymer solution with a pharmaceutically acceptable excipient. The aqueous polymer solution may comprise at least one AA-MA copolymer or a salt thereof in accordance with embodiments.

Kits and Other Articles of Manufacture

Also disclosed herein is a kit comprising the oral care composition, or the ingredients therefore, and an instructional material, which describes using the composition in a method of whitening a tooth. As used herein, an "instructional material," includes a publication, a recording, a diagram, or any other medium of expression which can be used to communicate the usefulness of the composition in a kit. The instructional material of the kit may, for example, be affixed to a container that contains the composition or be shipped together with a container which contains the composition. Alternatively, the instructional material may be shipped separately from the container with the intention that the recipient use the instructional material and the composition cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

In some embodiments, the kit may comprise at least one AA-MA copolymer or a salt thereof and a pharmaceutically acceptable excipient. The amount, composition and/or properties of the at least one AA-MA copolymer or salt thereof and of the pharmaceutically acceptable excipient may include any of the polymers and/or excipients discussed above.

In some embodiments, the kit may comprise one or more dispensers for the composition or useful for preparing the composition. In some embodiments, the kit may comprise one or more compartments and/or containers for the various constituents of the kit.

Optionally, the kit may further comprise an applicator. By the term "applicator," as the term is used herein, is meant any device including, but not limited to, a dental tray, a syringe, a pipette, a brush, a cup, and the like, suitable for contacting and/or treating the tooth surface with the composition.

ILLUSTRATIVE EXAMPLES

Example 1: Stain Prevention Study of Pure Polymers

Figure 1:
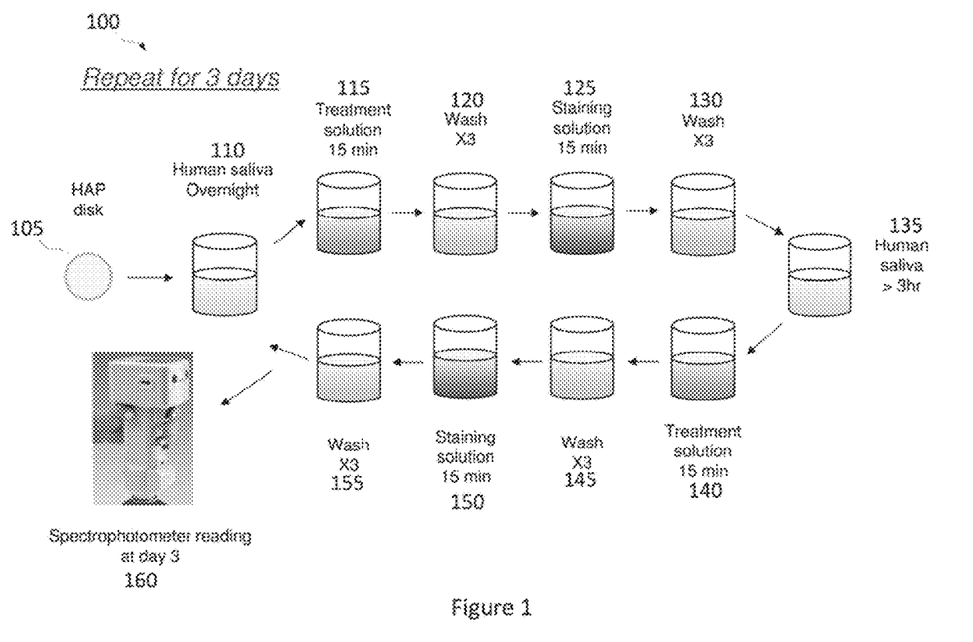
FIG. 1 depicts an experimental model used for evaluating the whitening benefits of various treatment solutions explored in the Examples.

FIG. 1 depicts an experimental model 100 used for evaluating the whitening benefits of various polymers. Hydroxyapatite (HAP) disks 105 were utilized to mimic a tooth surface. HAP disk 105 was submerged in human saliva overnight, in accordance with step 110. Subsequently, HAP disk 105 was treated with a treatment solution for 15 minutes, in accordance with step 115. The treatment solution contained about 2 wt % polymer solutions or deionized water as a control. The polymer solutions were 40 wt % aqueous polymer solutions. Thus, the treatment solution contained about 0.8 wt % polymer. The pH of the AA/MA Copolymer A, 2 wt % polymer solution, was about 8.31. The pH of the AA/MA Copolymer B, 2 wt % polymer solution, was about 8.40.

After treatment with a polymer solution, HAP disk 105 was washed three times with deionized water, in accordance with step 120. Thereafter, washed HAP disk 105 was submerged in a staining solution for 15 minutes, in accordance with step 125. The staining solution was prepared by steeping two tea bags in 100 mL of boiled deionized water. After staining, HAP disk 105 was washed three times with deionized water, in accordance with step 130.

Subsequently, washed HAP disk 105 was submerged in human saliva for about 3 hours or more, in accordance with step 135. Afterwards, steps 115 through 130 were repeated as depicted in steps 140 through 155. Specifically, HAP disk 105 was treated for 15 minutes with a treatment solution (step 140), washed three times with deionized water (step 145), submerged in a staining solution for 15 minutes (step 150), and washed three times with deionized water (step 155).

Steps 110 through 155 were intended to mimic an individual's daily hygienic routine of washing and/or brushing teeth twice daily. Steps 110 through 155 were repeated for three days. At the end of the third day, a spectrophotometer was utilized to assess the whitening performance of the various polymers studied, in accordance with step 160. The spectrophotometer was used to measure lightness and delta E*.

Figure 2A:
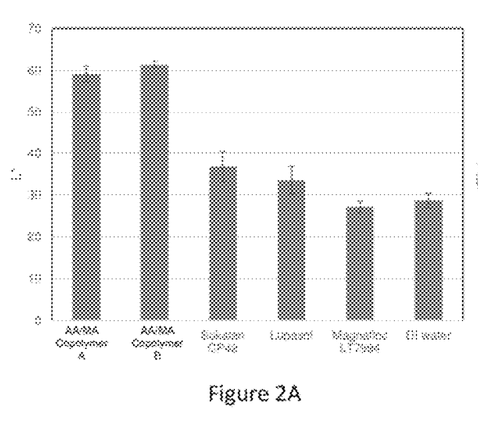
FIGS. 2A and 2B depict charts summarizing the lightness and delta E*ab, respectively, measured for HAP disks after treatment with treatment solutions.
Figure 2B:
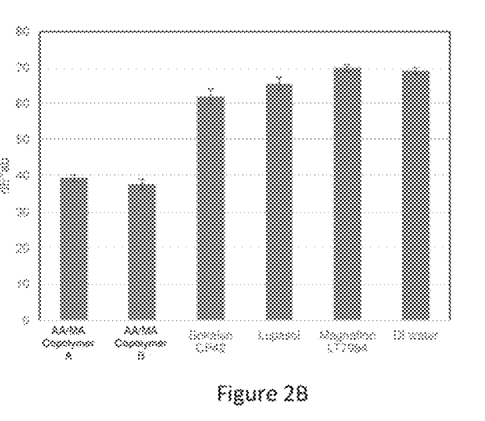

FIGS. 2A and 2B depict a chart summarizing the lightness and delta E*, respectively, measured for HAP disks after treatment with various polymers (AA/MA Copolymer A, AA/MA Copolymer B, Sokalan CP42, Lupasol, Magnafloc LT7994, DI Water). The compositions of the various polymers that were tested are as follows:

AA/MA Copolymer A: a sodium salt of an AA-MA copolymer having a molecular weight of 70,000 g/mol and a molar ratio of acrylic acid to maleic acid of 1:0.3.

AA/MA Copolymer B: a sodium salt of an AA-MA copolymer having a molecular weight of 50,000 g/mol and a molar ratio of acrylic acid to maleic acid of 1:0.6.

Sokalan CP42: a modified polycarboxylate sodium salt.

Lupasol: polyethyleneimines (branched spherical polymeric amines).

Magnafloc LT7994: cationic coagulant polyelectrolyte polymers.

As seen in FIG. 2A, the leading samples yielded a lightness L* of about 60, which is almost twice as much as was observed for the comparative polymers. As seen in FIG. 2B, the leading samples yielded a delta E* of about 40, which is almost 50% lower than the delta E* observed for comparative polymers. The best whitening effect was observed in HAP disks treated with polymer AA/MA Copolymer A and polymer AA/MA Copolymer B solutions.

Example 2: Stain Prevention Study of Polymers in Mouthwash

A study for evaluating the whitening benefits of various polymers in mouthwash (MW) was conducted in accordance with experimental model 100 illustrated in FIG. 1 and described in detail in Example 1. The treatment solutions studied here are listed in Table 1 below. Each treatment solution is associated with a code as summarized in Table 1 below.

TABLE 1

Treatment Solutions of Example 2

| Code | Description |
| --- | --- |
| A1 | Homemade MW with 2% AA/MA Copolymer A (without flavor) |
| B1 | Homemade MW with 2% AA/MA Copolymer B (without flavor) |
| A2 | Homemade MW with 2% AA/MA Copolymer A (with flavor) |
| B2 | Homemade MW with 2% AA/MA Copolymer B (with flavor) |
| A3 | Commercial MW A with 2% AA/MA Copolymer A |
| B3 | Commercial MW A with 2% AA/MA Copolymer B |
| A4 | Commercial MW B with 2% AA/MA Copolymer A |
| B4 | Commercial MW B with 2% AA/MA Copolymer B |
| L3 | Commercial MW A |
| L4 | Commercial MW B |
| DI water | DI water |

The pH of the AA/MA Copolymer A, 2 wt % polymer solution, was about 8.31. The pH of the AA/MA Copolymer B, 2 wt % polymer solution, was about 8.40. When the polymers were incorporated into a mouthwash formula, the pH was adjusted to about 5.5.

Figure 3A:
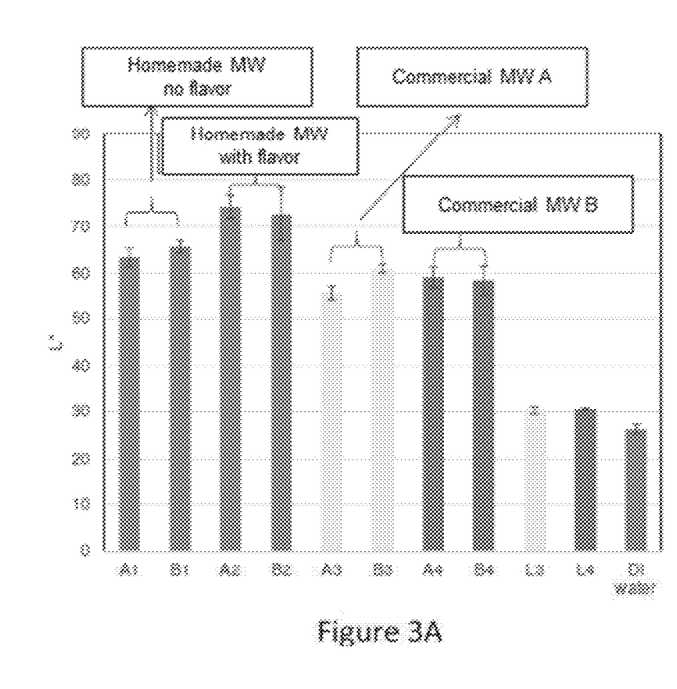
FIGS. 3A and 3B depict charts summarizing the lightness and delta E*, respectively, measured for HAP disks after treatment with various treatment solutions of Example 2.
Figure 3B:
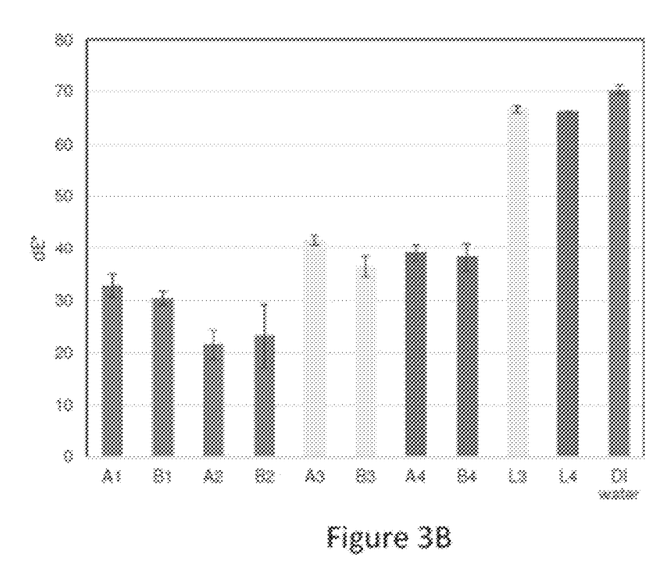

FIGS. 3A and 3B depict charts summarizing the lightness and delta E*, respectively, measured for HAP disks after treatment with various treatment solutions summarized in Table 1. As seen in FIG. 3A, the leading samples yielded a lightness L* of about 60 or greater, which is almost twice as much as was observed for the comparative treatment solutions, L3, L4, and deionized water. As seen in FIG. 3B, the leading samples yielded a delta E* of about 40 or less, which is almost 50% lower than the delta E* observed for comparative treatment solutions. L3, L4, and deionized water. The best whitening effect was observed for mouth wash samples which contained polymer AA/MA Copolymer A and/or polymer AA/MA Copolymer B (Codes A1, A2, A3, A4, B1, B2, B3, and B4). In fact, AA/MA Copolymer A and/or AA/MA Copolymer B show an improvement in whitening effects of commercial mouth wash products that are presently on the market.

From these results, it appears that AA/MA Copolymer A and/or AA/MA Copolymer B significantly improve the anti-staining performance of common commercial mouth washes.

Example 3: Stain Removal Study of Polymers with and without Pyrophosphates

A study for evaluating the stain removal ability of AA/MA Copolymer A and AA/MA Copolymer B with and without pyrophosphates as compared to pure hydrogen peroxide and hydrogen peroxide-containing mouthwash was conducted in accordance with experimental model 100 illustrated in FIG. 1 and described in detail in Example 1. The treatment solutions studied here are listed in Table 2 below. All treatment solutions had a pH of about 5.5.

TABLE 2

Treatment Solutions of Example 3

| Code | Description |
| --- | --- |
| Sample 1 | 2% AA/MA Copolymer B |
| Sample 2 | 2% AA/MA Copolymer A |
| Sample 3 | 1% H2O2 |
| Sample 4 | 2 wt % AA/MA Copolymer A + 1 wt % Potassium pyrophosphate + 1 wt % Sodium pyrophosphate |
| Sample 5 | 2 wt % AA/MA Copolymer B + 1 wt % Potassium pyrophosphate + 1 wt % Sodium pyrophosphate |
| Sample 6 | 1 wt % Potassium pyrophosphate + 1 wt % Sodium pyrophosphate |
| Sample 7 | Crest 3D White Luxe Glamorous mouthwash |
| DI water | DI water |

Figure 4A:
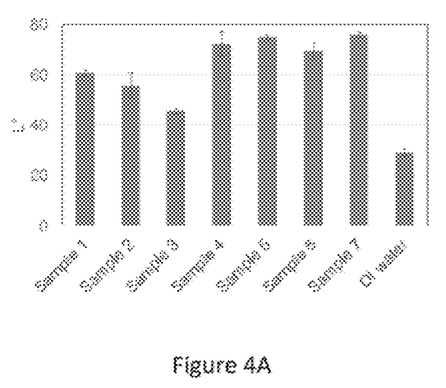
FIGS. 4A and 4B depict charts summarizing the lightness and delta E*, respectively, measured for HAP disks after treatment with various treatment solutions of Example 3.
Figure 4B:
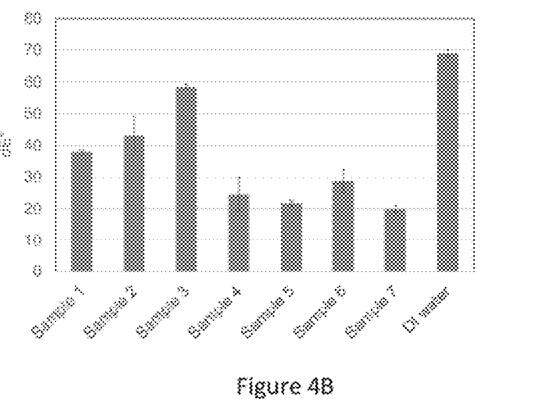

FIGS. 4A and 4B depict charts summarizing the lightness and delta E*, respectively, measured for HAP disks after treatment with various treatment solutions summarized in Table 2. As seen in FIG. 4A, the leading samples (containing pyrophosphates) yielded a lightness L* of about 70 or greater, which is slightly higher than the lightness observed for samples without pyrophosphates. As seen in FIG. 4B, the leading samples (containing pyrophosphates) yielded a delta E* of about 30 or less, which is lower than the delta E* observed for treatment solutions that did not include pyrophosphates. All treatment solutions show stain removal effect. Sample 7 shows the best performance. Samples containing pyrophosphates, samples 4 through 6, show better performance than samples 1 through 3.

From these results, it appears that AA/MA Copolymer A and/or AA/MA Copolymer B combined with pyrophosphates are efficacious in removing, preventing, or reducing existing stains from the tooth surface. In some instances, AA/MA Copolymer A and/or AA/MA Copolymer B are comparable to hydrogen peroxide and hydrogen peroxide-containing products in terms of their efficacy in removing, preventing, or reducing existing stains from the tooth surface.

Example 4: Stain Removal Study of Polymers with Toothpastes

A study for evaluating the stain removal benefits of AA/MA Copolymer A and AA/MA Copolymer B in toothpaste was conducted. The objective was to evaluate stain removal effects of commercial toothpastes as compared to homemade toothpastes containing AA/MA Copolymer A and/or AA/MA Copolymer B. The substrates used were stained bovine teeth.

The treatment solutions studied here are listed in Table 3 below. The treatment solutions were prepared as toothpaste slurries made with deionized water. The toothpaste slurries were prepared by mixing tooth paste and water at a toothpaste to water weight ratio of 1:2.

TABLE 3

Treatment Solutions of Example 4

| Sample | Description |
|---|---|
| Sample 1 | Homemade toothpaste with 2% AA/MA Copolymer A |
| Sample 2 | Homemade toothpaste with 2% AA/MA Copolymer B |
| Positive Control: Sample 3 | Colgate Enamel Health Whitening Toothpaste |
| Negative Control: Sample 4 | Placebo toothpaste |

The compositions of the toothpastes that were tested are summarized in Table 4 below:

TABLE 4

Compositions of Homemade Tested Toothpastes and Placebo

| Sample Name Ingredients | AA/MA Copolymer A Weight (%) | AA/MA Copolymer B Weight (%) | Placebo Weight (%) |
|---|---|---|---|
| Pluracare E 600 (PEG 12) | 3.00 | 3.00 | 3.00 |
| Xanthan Gum | 2 | 2 | 2 |
| Sodium Saccharin | 0.27 | 0.27 | 0.27 |
| Fluoride | 0.24 | 0.24 | 0.24 |
| Sorbitol | 56.4 | 56.4 | 56.4 |
| Zeodent 165 (thickener) | 10 | 10 | 10 |
| Zeodent 113 | 7.5 | 7.5 | 7.5 |
| Titanium Dioxide | 0.25 | 0.25 | 0.25 |
| Methyl Paraben | 0.1 | 0.1 | 0.1 |
| Propyl Paraben | 0.06 | 0.06 | 0.06 |
| Flavor | 0.9 | 0.9 | 0.9 |
| SLS | 1.5 | 1.5 | 1.5 |
| Polymer | 2% AA/MA Copolymer A | 2% AA/MA Copolymer B | 0 |
| Water | 15.78 | 15.78 | 17.78 |

The active ingredient of Colgate Enamel Health Whitening Toothpaste is listed as sodium fluoride. The inactive ingredients of Colgate Enamel Health Whitening Toothpaste are listed as: water, sorbitol, hydrated silica, glycerin, PEG-12, tetrasodium pyrophosphate, sodium lauryl sulfate, flavor, microcrystalline cellulose, zinc phosphate tetrahydrate, cellulose gum, cocamidopropyl betaine, sodium saccharin, xanthan gum, mica, and titanium dioxide. Thus, Colgate Enamel Health Whitening Toothpaste includes a pyrophosphate, namely a tetrasodium pyrophosphate.

Five replicates of each sample were prepared. Before grouping the bovine teeth, L*a*b* of the bovine teeth was measured and recorded. The bovine teeth were than grouped so that the average starting L* value of each group was about the same.

Bovine teeth were then mounted onto a brushing machine. Subsequently, toothpaste slurries were filled in the testing tubes and were also mounted onto the brushing machine. The brushing machine was set for 200 strokes in each cycle (i.e., the samples were subjected to 200 double strokes in each cycle). The brushing machine was operated for 14 cycles and the bovine teeth were removed and washed for color measurement.

Thereafter, the bovine teeth were mounted again onto the brushing machine for an additional 14 cycles. After the final 14 cycles, a final color measurement was conducted. The results that were obtained are summarized in Tables 5 through 8 below and in FIG. 5.

The lightness values L* observed for the five AA/MA Copolymer A samples are summarized in Table 5 below:

TABLE 5

Lightness (L*) of Bovine Teeth treated with a toothpaste slurry containing AA/MA Copolymer A

| Group 1 (Sample Numbers) | Baseline | 14 cycles | 28 cycles |
|---|---|---|---|
| 1 | 32.14 | 54.21 | 61.05 |
| 5 | 26.88 | 48.02 | 52.07 |
| 10 | 36.07 | 52.06 | 56.09 |
| 8 | 31.27 | 52.28 | 58.16 |
| 19 | 29.34 | 48.78 | 57.94 |
| Average | 31.14 | 51.07 | 57.062 |
| Standard Deviation | 3.417214 | 2.590869 | 3.307018 |

The lightness values L* observed for the five AA/MA Copolymer B samples are summarized in Table 6 below:

TABLE 6

Lightness (L*) of Bovine Teeth treated with a toothpaste slurry containing AA/MA Copolymer B

| Group 2 (Sample Numbers) | Baseline | 14 cycles | 28 cycles |
|---|---|---|---|
| 2 | 31.59 | 58.47 | 62.39 |
| 6 | 34.04 | 58.98 | 63.61 |
| 16 | 24.99 | 57.48 | 63.74 |
| 13 | 39.6 | 63.14 | 65.4 |
| 20 | 27.8 | 56.32 | 63.09 |
| Average | 31.604 | 58.878 | 63.646 |
| Standard Deviation | 5.658748 | 2.590332 | 1.115047 |

The lightness values L* observed for the five placebo samples (negative control) are summarized in Table 7 below:

TABLE 7

Lightness (L*) of Bovine Teeth treated with a placebo toothpaste slurry

| Group 3 (Sample Numbers) | Baseline | 14 cycles | 28 cycles |
|---|---|---|---|
| 3 | 30.53 | 50.25 | 52.85 |
| 7 | 33.18 | 47.93 | 54.07 |
| 14 | 29.72 | 52.18 | 54.69 |
| 15 | 29.39 | 50.83 | 53.09 |
| 17 | 32.29 | 49.36 | 52.1 |
| Average | 31.022 | 50.11 | 53.36 |
| Standard Deviation | 1.648141 | 1.591996 | 1.023914 |

The lightness values L* observed for the five samples containing Colgate Enamel Health Whitening Toothpaste (positive control) are summarized in Table 8 below:

TABLE 8

Lightness (L*) of Bovine Teeth treated with a
Colgate Enamel Health Whitening
Toothpaste slurry

| Group 4 (Sample Numbers) | Baseline | 14 cycles | 28 cycles |
|---|---|---|---|
| 4 | 30.05 | 62.74 | 65.35 |
| 9 | 34.19 | 62.25 | 64.01 |
| 18 | 24.88 | 60.86 | 63.46 |
| 11 | 32.3 | 60.34 | 65.52 |
| 12 | 33.79 | 62.05 | 64.53 |
| Average | 31.042 | 61.648 | 64.574 |
| Standard Deviation | 3.80783 | 1.006017 | 0.874374 |

Figure 5:
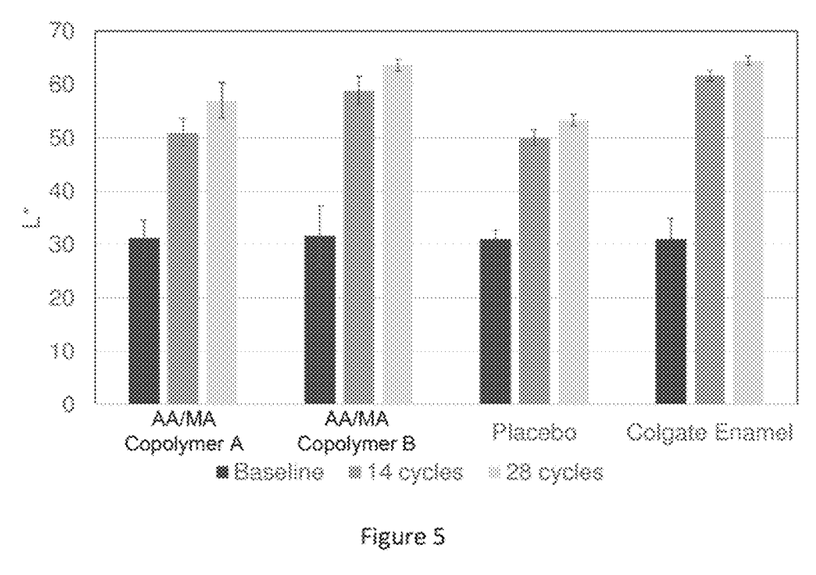
FIG. 5 depicts a chart summarizing the lightness measured for bovine teeth after treatment with various treatment solutions of Example 4.

FIG. 5 depicts a chart summarizing the average lightness (L*) measured for bovine teeth after treatment with various treatment solutions summarized in Table 3. As seen in FIG. 5, all toothpaste samples show a good stain-removal effect. The lightness (L*) significantly increases after 14 cycles and additional 14 cycles of brushing increase the lightness (L*) slightly more.

When compared to the placebo. AA/MA Copolymer A and AA/MA Copolymer B show moderately better stain removal effect. The stain-removal performance of the various samples may be summarized as follows:

| Colgate Enamel toothpaste | > | AA/MA Copolymer B toothpaste | > | AA/MA Copolymer A toothpaste | > | Placebo Toothpaste |
|---|---|---|---|---|---|---| where Colgate Enamel Toothpaste showed the greatest stain removal effect and the placebo toothpaste showed the lowest stain removal effect.

FIG. 5 also shows that the AA/MA Copolymer B toothpaste resulted in similar results to Colgate enamel toothpaste after 28 cycles.

For simplicity of explanation, the embodiments of the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events.

In the foregoing description, numerous specific details are set forth, such as specific materials, dimensions, processes parameters, etc., to provide a thorough understanding of the present invention. The particular features, structures, materials, or characteristics may be combined in any suitable manner in one or more embodiments. The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an embodiment", "certain embodiments", or "one embodiment" means that a particular feature, structure, or characteristic described in connection with the embodiment is included in at least one embodiment. Thus, the appearances of the phrase "an embodiment", "certain embodiments", or "one embodiment" in various places throughout this specification are not necessarily all referring to the same embodiment.

Reference throughout this specification to numerical ranges should not be construed as limiting and should be understood as encompassing the outer limits of the range as well as each number and/or narrower range within the enumerated numerical range.

The term "about", when referring to a physical quantity, is to be understood to include measurement errors within, and inclusive of 10%. For example, "about 100° C." should be understood to mean "100±10° C.".

As used herein. "tooth whitening" refers to a lightening of tooth shade relative to the tooth shade prior to treatment. Lightening is assessed on an isolated or an in situ tooth by standard, art-recognized methods of assessing tooth shade, which include qualitative, quantitative and semi-quantitative methods. For instance, lightening may be assessed by simple visual inspection. e.g., by comparing "before" and "after" photographs of the treated teeth. Alternatively, a tooth may be deemed whitened when the tooth shade relative to the tooth shade prior to treatment is two or more shades lighter, as assessed by Vita classical shade guide (preferably, under controlled visible light conditions) or two or more levels as assessed using the Vita Bleachedguide 3D-MASTER Shade system, which utilizes a multiple color spectrophotometer and includes half lightness levels.

The term "yields" refers to the resulting lightness (L*) and/or delta E* produced after treating HAP disks with various treatment solutions pursuant to experimental model 100.

As used herein, an "effective amount" of at least one AA-MA copolymer is intended to mean any amount of AA-MA copolymer that will result in tooth whitening, as defined herein, using methods of assessment known to the skilled artisan, as discussed above of a tooth, with one or more treatments.

A "thickener," as the phrase is used herein, refers to a component that has the property of thickening a solution or mixture to which it is added.

The present invention has been described with reference to specific exemplary embodiments thereof. The specification and drawings are, accordingly, to be regarded in an illustrative rather than a restrictive sense. Various modifications of the invention in addition to those shown and described herein will become apparent to those skilled in the art and are intended to fall within the scope of the appended claims.

What is claimed is:

1. An oral care composition comprising:
    an effective amount of at least one acrylic acid-maleic acid (AA-MA) copolymer or a salt thereof to prevent or minimize formation of stains on a tooth surface or to remove or reduce existing stains from a tooth surface, wherein the at least one AA-MA copolymer or a salt thereof is included in an amount of about 0.5 wt % to about 2 wt %, a pharmaceutically acceptable excipient, wherein the pharmaceutically acceptable excipient comprises a solvent, a thickener, a buffer, a humectant, a surfactant, an abrasive, a sweetener, a flavorant, a pigment, a dye, an anti-caries agent, a whitening agent, a desensitizing agent, a preservative, or a mixture thereof; and an aqueous polymer solution, wherein the aqueous polymer solution comprises 20%-60% by weight of the at least one AA-MA copolymer or a salt thereof based on total weight of the aqueous polymer solution, and wherein the at least one AA-MA copolymer has a molecular weight ranging from about 50,000 g/mol to about 70,000 g/mol, wherein the oral care composition causes a lightness $L^*$ of about 60 to about 95 and a delta $E^*$ of about 20 to about 40 to the tooth surface.

2. The oral care composition of claim 1, wherein the at least one AA-MA copolymer or salt thereof consists of at least one sodium salt of an AA-MA copolymer, at least one potassium salt of an AA-MA copolymer, or a combination thereof.

3. The oral composition of claim 1, wherein the molar ratio of AA to MA in the at least one AA-MA copolymer ranges from about 1:10 to about 10:1.

4. The oral care composition of claim 1, having a pH ranging from about 5 to about 9.

5. The oral care composition of claim 1, wherein the oral care composition is a mouth wash, a toothpaste, an orally dissolving strip, a whitening gel, a whitening wrap, a whitening cream, or a whitening ointment.

6. The oral composition of claim 1, wherein the pharmaceutically acceptable excipient comprises from about 0.5 wt % to about 5 wt % pyrophosphates or salts thereof.

7. The oral composition of claim 6, wherein the pyrophosphates or salts thereof consists of sodium pyrophosphate, potassium pyrophosphate, or a combination thereof.

8. A method for preventing or minimizing stain formation on a tooth surface or for removing or reducing existing stains from the tooth surface, the method comprising treating the tooth surface with an oral care composition of claim 1 to prevent or minimize stain formation on the tooth surface or to remove or reduce existing stains from the tooth surface.

9. The method of claim 8, wherein the oral care composition comprises at least one sodium salt of an AA-MA copolymer, at least one potassium salt of an AA-MA copolymer, or a combination thereof, wherein the at least one AA-MA copolymer has a molecular weight ranging from about 50,000 g/mol to about 70,000 g/mol, wherein the molar ratio of AA to MA in the at least one AA-MA copolymer ranges from about 1:10 to about 10:1, and wherein the oral care composition comprises from about 0.5 wt % to about 2 wt % of the at least one AA-MA copolymer or a salt thereof based on total weight of the oral care composition.

10. The method of claim 8, wherein the oral care composition is a mouth wash, a toothpaste, an orally dissolving strip, a whitening gel, a whitening wrap, a whitening cream, or a whitening ointment, and wherein the oral care composition has a pH ranging from about 5 to about 9.

11. The method of claim 8, wherein the pharmaceutically acceptable excipient comprises from about 0.5 wt % to about 5 wt % pyrophosphates or salts thereof, and wherein the pyrophosphates or salts thereof comprise sodium pyrophosphate, potassium pyrophosphate, or a combination thereof.

12. The method of claim 8, wherein treating comprises applying, brushing, rinsing, spraying, pouring, and combinations thereof.

13. A method for preparing an oral care composition of claim 1, the method comprising:

forming an aqueous polymer solution comprising at least one acrylic acid-maleic acid (AA-MA) copolymer or a salt thereof; and combining the aqueous polymer solution with a pharmaceutically acceptable excipient.

* * * * *